United States Patent
Esposito

(10) Patent No.: US 10,909,646 B2
(45) Date of Patent: Feb. 2, 2021

(54) EQUITABLY ASSIGNING MEDICAL IMAGES FOR EXAMINATION

(71) Applicant: PACS HARMONY, LLC, Brandon, FL (US)

(72) Inventor: Michael B. Esposito, Brandon, FL (US)

(73) Assignee: PACS HARMONY, LLC, Brandon, FL (US)

( * ) Notice: Subject to any disclaimer, the term of this patent is extended or adjusted under 35 U.S.C. 154(b) by 708 days.

(21) Appl. No.: 15/670,588

(22) Filed: Aug. 7, 2017

(65) Prior Publication Data
US 2017/0358047 A1     Dec. 14, 2017

Related U.S. Application Data

(63) Continuation of application No. 12/362,197, filed on Jan. 29, 2009, now Pat. No. 9,727,935.

(51) Int. Cl.
    G16H 30/20     (2018.01)
    G06Q 50/22     (2018.01)
    G06Q 10/06     (2012.01)

(52) U.S. Cl.
    CPC ............ *G06Q 50/22* (2013.01); *G06Q 10/06* (2013.01); *G06Q 10/0631* (2013.01)

(58) Field of Classification Search
    CPC ................................................ G06Q 50/22–24
    See application file for complete search history.

(56) References Cited

U.S. PATENT DOCUMENTS

| 5,321,520 A | 6/1994 | Inga et al. |
|---|---|---|
| 6,006,191 A | 12/1999 | DiRienzo |
| 6,260,021 B1 | 7/2001 | Wong et al. |
| 6,269,379 B1 | 7/2001 | Hiyama et al. |
| 6,675,271 B1 | 1/2004 | Xu et al. |
| 6,678,703 B2 | 1/2004 | Rothschild et al. |
| 8,065,166 B2 | 11/2011 | Maresh et al. |
| 9,727,935 B2 * | 8/2017 | Esposito ............... G06Q 10/06 |

(Continued)

FOREIGN PATENT DOCUMENTS

WO     2008052283 A1     5/2008

OTHER PUBLICATIONS

International Search Report and Written Opinion for PCT/US2009/068434 dated Feb. 25, 2010.

*Primary Examiner* — Robert A Sorey

(74) *Attorney, Agent, or Firm* — Thomas | Horstemeyer, LLP

(57) ABSTRACT

Disclosed are various embodiments for equitably assigning medical images for examination. Data describing medical image studies pending examination are obtained from a medical data server. A relative complexity value is determined for each of the medical image studies based on an average amount of time to perform a particular type of image study. The medical image studies are assigned for examination by a respective user based on preferences associated with the respective user and the relative complexity value determined for each medical image study. A user interface is rendered by a client device, where the user interface includes a respective user worklist for each user. A user is prevented from viewing a particular medical image study based on a lock status associated with the particular medical image study.

20 Claims, 5 Drawing Sheets

(56)  References Cited

U.S. PATENT DOCUMENTS

| | | |
|---|---|---|
| 2002/0087444 A1 | 7/2002 | DiPiero et al. |
| 2005/0242946 A1 | 11/2005 | Hubbard, Jr. et al. |
| 2006/0195339 A1 | 8/2006 | Backhaus et al. |
| 2007/0067247 A1 | 3/2007 | Brookhart |
| 2007/0143136 A1 | 6/2007 | Moore et al. |
| 2007/0225921 A1 | 9/2007 | Gutman |
| 2008/0118119 A1 | 5/2008 | Mahesh et al. |
| 2008/0140454 A1* | 6/2008 | Hernandez ............ G06F 19/321 705/3 |
| 2008/0312963 A1 | 12/2008 | Reiner |
| 2009/0047648 A1 | 2/2009 | Ferreira |
| 2009/0216556 A1 | 8/2009 | Martin et al. |
| 2010/0054566 A1 | 3/2010 | Toda |
| 2010/0114597 A1 | 5/2010 | Shreiber et al. |

* cited by examiner

| | Username | Start Date | Start Time | End Date |
|---|---|---|---|---|
| | Rad1 | 12/1/2007 | 0800 | 12/20/2007 |
| ▶ | Rad2 | 12/3/2007 | 0800 | 12/20/2007 |
| | Rad3 | 12/5/2007 | 0800 | 12/15/2007 |
| | | | | |

Radiologist Schedule

EQUITABLY ASSIGNING MEDICAL IMAGES FOR EXAMINATION

CROSS-REFERENCE TO RELATED APPLICATIONS

This application is a continuation of, and claims priority to, U.S. Patent Application entitled "EQUITABLY ASSIGNING MEDICAL IMAGES FOR EXAMINATION," filed on Jan. 29, 2009, and assigned application Ser. No. 12/362,197, which is incorporated herein by reference in its entirety.

BACKGROUND

Many modalities, or methods, exist for the creation of images to be used in medical diagnosis and treatment. These modalities include radiography, or X-ray imaging, computed tomography (CT), magnetic resonance imaging (MRI), ultrasound, mammography, nuclear medicine, positron emission tomography (PET), and other modalities. The images produced as a result of these modalities are carefully examined by specialists having advanced training, such as radiologists.

In recent years, digital technology has made possible a shift from hard copy distribution of medical images for examination to digital distribution. Digital distribution of medical images is typically performed by picture archiving and communications systems (PACS). PACS comprise computers or networks dedicated to the storage, retrieval, distribution, and presentation of medical images. The medical images are stored in a format such as the digital imaging and communications in medicine (DICOM) standard. The use of PACS has also enabled teleradiology, whereby a radiologist or other specialist may examine a medical image and associated patient data at an off-site location.

SUMMARY OF THE INVENTION

Briefly described, one embodiment, among others, is a system comprising at least one computing device and a medical image study assignment application executable in the at least one computing device. When executed the medical image study assignment application causes the at least one computing device to at least perform the following. The medical image study assignment application obtains data describing a plurality of medical image studies from at least one medical data server, where the plurality of medical image studies are pending examination. The medical image study assignment application determines a relative complexity value for each of the plurality of medical image studies based at least in part on an average amount of time to perform a particular type of image study. The medical image study assignment application assigns each of the plurality of medical image studies for examination by a respective user of a plurality of users based at least in part on preferences associated with the respective user and the relative complexity value determined for each of the plurality of medical image studies. The medical image study assignment application causes a user interface to be rendered by a client device, the user interface including a respective user worklist for each of the plurality of users. The medical image study assignment application prevents a user from viewing a particular medical image study based at least in part on a lock status associated with the particular medical image study by at least preventing access to image data associated with the particular medical image study stored in a data store.

Another embodiment is a computer-implemented method comprising the following steps. The method comprises obtaining data describing a plurality of medical image studies from at least one medical data server, the plurality of medical image studies pending examination. The method further comprises determining a relative complexity value for each of the plurality of medical image studies based at least in part on an average amount of time to perform a particular type of image study. The method further comprises assigning each of the plurality of medical image studies for examination by a respective user of a plurality of users based at least in part on preferences associated with the respective user and the relative complexity value determined for each of the plurality of medical image studies. The method further comprises causing a user interface to be rendered by a client device, the user interface including a respective user worklist for each of the plurality of users. The method further comprises preventing a user from viewing a particular medical image study based at least in part on a lock status associated with the particular medical image study by at least preventing access to image data associated with the particular medical image study stored in a data store.

Another embodiment is a non-transitory computer-readable medium embodying a program executable in at least one computing device, wherein when executed the program causes the at least one computing device to at least perform the following. The program obtains data describing a plurality of medical image studies from at least one medical data server, the plurality of medical image studies pending examination. The program determines a relative complexity value for each of the plurality of medical image studies based at least in part on an average amount of time to perform a particular type of image study. The program assigns each of the plurality of medical image studies for examination by a respective user of a plurality of users based at least in part on preferences associated with the respective user and the relative complexity value determined for each of the plurality of medical image studies. The program causes a user interface to be rendered by a client device, the user interface including a respective user worklist for each of the plurality of users. The program prevents a user from viewing a particular medical image study based at least in part on a lock status associated with the particular medical image study by at least preventing access to image data associated with the particular medical image study stored in a data store.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

DETAILED DESCRIPTION

A PACS system typically has one list of medical image studies pending distribution for all users of the PACS system. A physician, such as a radiologist or other specialist, may access the PACS system to choose medical image studies to work on through the PACS system. Often, however, this results in an inequitable assignment of work. For example, a physician might select for himself all of one type of easier studies while leaving the others to do the more difficult studies that remain. As another example, a physician might select too many studies, leaving the others with little or no work. Consequently, with a standard PACS system, efficient physicians become frustrated with the unequal workload, and more deliberative physicians feel stressed to complete assignments in a short amount of time.

The medical image assignment system described herein solves these problems by generating multiple worklists, one for each physician or user, and equitably distributing patient studies automatically to the worklist of each user. Studies may be distributed, for example, based upon configured preferences for the users, an estimated completion time associated with each study, a payment associated with each study, one or more comparison metrics associated with each case, and/or other factors. In the following discussion, a general description of the medical image assignment system and its components is provided, followed by a discussion of the operation of the same.

Figure 1:
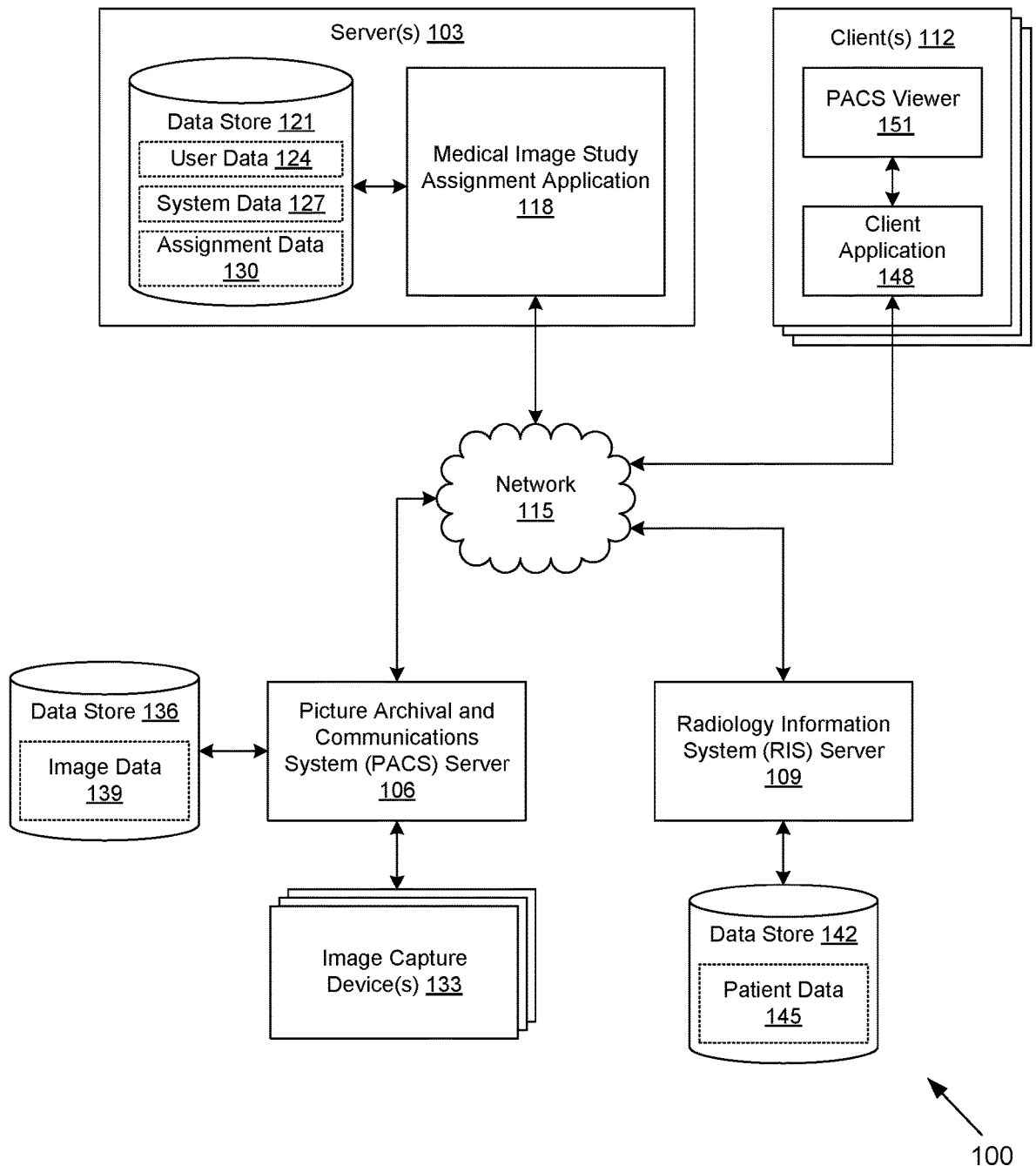
FIG. 1 is a drawing of a networked environment according to an embodiment of the present disclosure.

With reference to FIG. 1, shown is a networked environment 100 according to various embodiments of the present disclosure. The networked environment 100 includes one or more servers 103 that are in data communication with one or more PACS servers 106, one or more Radiology Information System (RIS) servers 109, and one or more clients 112 by way of a network 115. The network 115 includes, for example, the Internet, intranets, extranets, wide area networks (WANs), local area networks (LANs), wired networks, wireless networks, or other suitable networks, etc., or any combination of two or more such networks.

The server 103 may comprise, for example, a server computer or like system. The server 103 may represent multiple servers arranged, for example, in one or more server banks or other arrangements. Such servers may be located in a single installation or may be dispersed among many different geographical locations. For purposes of convenience, the server 103 is referred to herein in the singular. However, in one embodiment, the server 103 represents a plurality of servers arranged as described above.

The server 103 includes medical image study assignment application 118, a data store 121, and potentially other applications and data. The medical image study assignment application 118 may be employed to assign medical image studies to users. The data store 121 may be used to store data including user data 124, system data 127, assignment data 130, and other data. The data store 121 may comprise a relational database management system such as MySQL or another system.

User data 124 may contain data relating to users, such as schedules, locations, preferences, security credentials, and other data. System data 127 may contain data relating to system configuration, such as settings required to interface with a PACS server 106 or an RIS server 109 and other data. Assignment data 130 may contain data describing assignments of medical image studies to users, including information received from a PACS server 106 and/or an RIS server 109 about particular medical image studies, status and other information provided by a client 112 regarding the examination of a medical image study, etc.

The PACS server 106 may comprise, for example, a server computer or like system. The PACS server 106 may represent multiple servers arranged, for example, in one or more server banks or other arrangements. Such servers may be located in a single installation or may be dispersed among many different geographical locations. For purposes of convenience, the PACS server 106 is referred to herein in the singular. However, in one embodiment, the PACS server 106 represents a plurality of servers arranged as described above. The PACS server 106 executes applications and performs functions associated with a PACS as is known in the art. The PACS server 106 may be a commercially available PACS provided by commercial vendors, such as GE, AGFA, Siemens, Philips, McKesson, Fuji, Amicas, and/or other vendors.

The PACS server 106 may provide images and other data associated with a medical image study. The PACS server 106 may be in data communication with one or more image capture devices 133 configured to create medical images. The image capture devices 133 may provide medical images of patients for any modality, such as radiography, or X-ray imaging, computed tomography, magnetic resonance imaging, ultrasound, mammography, nuclear medicine, positron emission tomography, and/or other modalities. The PACS server 106 may be configured to receive user input to describe the acquired medical images by way of input devices and/or clients over a data communications network. The PACS server 106 may be capable of exchanging patient-related information over a data communications network such as network 115 through, as a nonlimiting example, a Health Level 7 (HL7) interface.

The PACS server 106 may be in data communication with a data store 136. In other embodiments, the data store 136 may reside on one or more PACS servers 106. The data store 136 may be used to store data including image data 139 and other data. Image data 139 may contain data relating to the acquired medical images, metadata, and other data. In particular, medical images comprising a medical image study may be stored in the image data 139 in a format such as, for example, DICOM.

The RIS server 109 may comprise, for example, a server computer or like system. The RIS server 109 may represent multiple servers arranged, for example, in one or more server banks or other arrangements. Such servers may be located in a single installation or may be dispersed among many different geographical locations. For purposes of convenience, the RIS server 109 is referred to herein in the singular. However, in one embodiment, the RIS server 109 represents a plurality of servers arranged as described above. The RIS server 109 executes applications and performs functions associated with an RIS as is known in the art. The RIS server 109 may be a commercially available RIS provided by commercial vendors, such as GE, AGFA, Siemens, Philips, McKesson, Fuji, Amicas, and/or other vendors.

The RIS server 109 may be used, for example, to store, manipulate, and distribute patient radiological data and imagery. Applications executable on the RIS server 109 may enable features such as, for example, patient registration and appointment entry, patient tracking and scheduling, result reporting, image tracking, and other features. The RIS server 109 may be configured to receive user input by way of input devices and/or clients over a data communications network.

The RIS server 109 may be in data communication with a data store 142. In other embodiments, the data store 142 may reside on one or more RIS servers 109. The data store 142 may be used to store data including patient data 145 and other data. Patient data 145 may contain data relating to patient information, appointments, patient history, medical image studies, and other data.

The RIS server 109 may be in data communication with one or more PACS servers 106 by way of the network 115 or some other network. The RIS server 109 may exchange, for example, HL7 data concerning medical image studies with the PACS server 106. In some embodiments, the RIS server 109 and the PACS server 106 may reside on the same server or group of servers. In particular, a vendor may design a combined RIS/PACS system performing the same functionality of the PACS server 106 and the RIS server 109. Both the PACS server 106 and the RIS server 109 may be referred to broadly as "medical data servers."

Each of the clients 112 may comprise, for example, a computer system such as a desktop, laptop, or other computer system. The clients 112 may also comprise personal digital assistants, cellular telephones, set-top boxes, or other systems with like capability. Further, the clients 112 may also comprise any device that is network capable that may communicate with the server 103 over the network 115 to perform various functions. Such clients 112 may comprise, for example, processor-based devices having processor circuits comprising a processor and a memory.

The clients 112 may be configured to execute various applications such as a client application 148, a PACS viewer 151, and/or other applications. The client application 148, which may be a browser or some other thin or thick client application, may be executed in a client 112, for example, to access and render web pages or other network content served up by the server 103 or other servers. The client application 148 may be capable of interfacing with the PACS server 106 and/or the RIS server 109 to retrieve, view, and/or modify DICOM images and/or other data. In some embodiments, the PACS viewer 151 may be present to interface with the PACS server 106 to retrieve, view, and/or modify DICOM images and/or other data.

The clients 112 may be connected to one or more peripheral devices. In particular, peripheral devices may include input devices, for example, a keyboard, keypad, touch pad, touch screen, microphone, scanner, mouse, joystick, or one or more push buttons, etc. The peripheral devices may also include display devices, indicator lights, speakers, printers, etc. Specific display devices may be, for example, cathode ray tubes (CRTs), liquid crystal display (LCD) screens, gas plasma-based flat panel displays, LCD projectors, or other types of display devices, etc.

Next, a general description of the operation of the various components of the networked environment 100 is provided. Data relating to a patient, which may include appointment data, medical background data, and other data, is entered into the RIS server 109 and stored in patient data 145. A patient undergoes a medical image study at a hospital or other clinic, and the PACS server 106 obtains medical images comprising the medical image study from the image capture devices 133. The PACS server 106 then stores data relating to the medical image study in image data 139. The data may be, for example, DICOM images. The PACS server 106 may exchange data through an HL7 interface with the RIS server 109.

The PACS server 106 and/or the RIS server 109 may be configured to notify the medical image study assignment application 118 on the server 103 that a new medical image study is available. Such a medical image study may be completed with images, in progress, or have some other status. As an alternative, the medical image study assignment application 118 may be configured to poll the PACS server 106 and/or the RIS server 109 for updates relating to medical image study data. Either way, the medical image study assignment application 118 obtains data describing at least one medical image study from at least one medical data server, where the medical image study has yet to be examined by a user.

The medical image study assignment application 118 may authenticate a client application 148 on a client 112 for configuration of settings. A client application 148 may provide security credentials such as a username and/or password or other security credentials. Certain configuration settings may, in some embodiments, be configurable only by an administrator user. Configuration settings may involve establishing user accounts, setting user preferences and other user settings such as location, work schedule, etc. Configuration settings may also involve network communication and other settings to enable the medical image study assignment application 118 to communicate with one or more medical data servers such as PACS server 106 or RIS server 109. As a nonlimiting example, the medical image study assignment application 118 may communicate with a PACS server 106 by obtaining DICOM data files. As another nonlimiting example, the medical image study assignment application 118 may communicate with an RIS server 109 by obtaining HL7 data over an HL7 interface such as the Mirth HL7 interface engine. The HL7 data may include observation results/unsolicited (ORU) messages, order messages (ORM), and other data.

The data describing a medical image study may include fields such as patient name, referring physician, exam, or institution, code, exam description, history or the reason for the study, STAT, or emergency, designation, status, accession number, or study unique identifier, medical record number, or patient unique identifier, and/or other fields. Some of these fields may be determined wholly by the medical image study assignment application 118, in some cases based on other fields or internal or external data.

Upon receiving data describing one or more medical image studies that are pending examination, the medical image study assignment application 118 proceeds to assign the medical image study or studies for examination by one or more users. To begin with, the medical image study assignment application 118 calculates a relative complexity value or weight for each medical image study.

The relative complexity value may be determined in part by a quantity of relative value units (RVU) associated with the particular type of medical image study. One purpose of the RVU is to pay the correct amount for each medical image study based on the amount of time spent on each medical image study. One example is a CT scan of a chest as compared with a chest x-ray. The CT scan may take five times longer to read on the average and therefore may have a payment that is five times greater. The RVUs may be determined based on standards set by another organization, such as, for example, the Medicare relative value scale. RVUs may also be locally configured for an institution through the client application 148 and stored in system data 127.

The assignments may also be determined in part based upon a number of user preferences and other factors through the use of a number of coefficients, including a user modality preference coefficient, a user subspecialty preference coefficient, a location coefficient, and other coefficients. The user modality preference may relate to preferred modalities including computed tomography, magnetic resonance imaging, mammography, nuclear medicine, radiography, positron emission tomography, ultrasound, and/or other modalities. The user subspecialty preference may reflect subspecialties such as neuro, body, or other subspecialities. The coefficients associated with the preferences may range, as a nonlimiting example, from 0 to 10 for each user. In this example, a setting of 10 may indicate that the user is able to receive all of the work normally available to the user for that modality, subspecialty, location, etc., while a setting of 0 may indicate that the user should never receive work associated with that modality, subspecialty, location, etc.

The coefficients and other user-related data may be stored, for example, in user data 124. The applicable coefficients and the relative complexity values are used by the medical image study assignment application 118 in calculating a final relative weight for the medical image study. In one embodiment, the assignments and calculations of final relative weights may not be performed until all medical images in a study have been received in the PACS server 106 and the study has been documented as having been completed by the technologist and ready for examination.

Once the final relative weights have been calculated for a medical image study, the medical image study assignment application 118 assigns the medical image study to a user or to multiple users. The assignments may be stored in assignment data 130. The assignments are thus made in an equitable fashion based upon the relative complexity values and the configured preferences and other factors instead of first-come, first-served or other methods that may result in inequitable distribution of the workload.

Once the assignments are made, data describing the assignments may be sent to a client application 148 on a client 112 over a network 115. The sending of data may be prompted by a request by the client application 148 or may be automatic to push the data to the client application 148. The communication over the network 115 may be performed using hypertext transfer protocol (HTTP), secure HTTP, simple object access protocol (SOAP), and/or some other protocol suitable for transmitting data over the network 115.

The client application 148 is configured to display worklists to the users, with each worklist being associated with a user and describing the medical image studies that have been assigned to the user for examination. In some embodiments, a user that has been authenticated on the client application 148 may only be able to see only his or her own worklist. Alternatively, a user may be able to see all worklists. The client application 148 may be configured to launch a PACS viewer 151 to view medical images on the PACS server 106 based upon a particular medical image study that has been selected to be examined by the user. In some embodiments, the viewer may be an integral component of client application 148. The client application 148 may also be configured to obtain additional data about the medical image study from an RIS server 109 or to modify data on the RIS server 109 or PACS server 106 regarding the medical image study. The client application 148 may also display a worklist containing medical image studies that have not been assigned because they have yet to be completed or are otherwise not ready for examination.

The client application 148 may display the status associated with each medical image study within a worklist and may also allow for the modification of the status as it changes. Statuses may include completed, scheduled, in progress, and other statuses. The client application 148 may also send a lock status to let other users know that someone else is examining a particular medical image study. Such a lock status may be used to prevent other users from examining locked medical images studies. The client application 148 may be configured to send the data over the network 115 to the server 103 or to a medical data server such as the RIS server 109 or the PACS server 106.

In some embodiments, the client application 148 may be configured as a portal adapted to other needs of the users. It may be configurable to display, for example, stock tables, weather and sports updates, etc. As a nonlimiting example, the client application 148 may display a clock that will count down minutes, days, and hours to events such as vacation, the weekend, retirement, and other events. These additional features would minimize the need to open other applications on the client 112.

In one embodiment, the client 112 may be merged with the server 103 into a single computer system. The functionality of the medical image study assignment application 118 and the client application 148 may thus be performed by a single application if desired. Furthermore, the medical image study assignment application 118 may also reside on the PACS server 106 or the RIS server 109 in some cases. There are many such variations of hardware configurations that may suit a particular deployment of the networked environment 100.

Figures 2, 3:
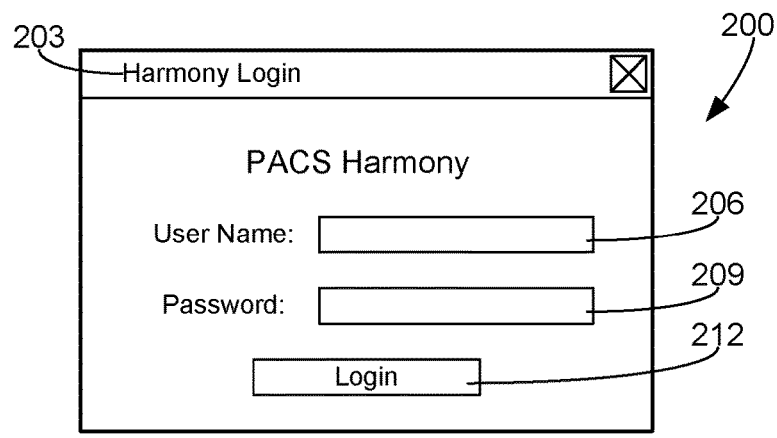
FIGS. 2-4 are drawings of example user interfaces for a client application employed in the networked environment of FIG. 1 according to an embodiment of the present disclosure.

Moving now to FIG. 2, shown is one example of a user interface 200 used in an embodiment of the client application 148 (FIG. 1). The user interface 200 as shown enables a user of the client 112 (FIG. 1) to log in and become authenticated with the medical image study assignment application 118 (FIG. 1) executing on the server 103 (FIG. 1).

The user interface 200 has a title bar 203, which, in this embodiment, features the title, "Harmony Login." The user interface 200 also features a user name input field 206, a password input field 209, and a login button 212. A user may fill in a user name in the user name input field 206, a password in the password input field 209, and then click the login button 212 to become authenticated with the medical image study assignment application 118. In the case of an authentication failure, such as an incorrect user name or password, the user interface 200 may prompt the user to try again or may become disabled upon repeated failures. In some embodiments, authentication may be unnecessary and/or require more or less information to be supplied by the user.

Turning now to FIG. 3, shown is one example of a user interface 300 used in an embodiment of the client application 148 (FIG. 1). The user interface 300 as shown enables a user of the client 112 (FIG. 1) to view and change settings of the medical image study assignment application 118 (FIG. 1) executing on the server 103 (FIG. 1). In this embodiment, the user interface 300 shows, in particular, a table of settings related to user work schedules.

The user interface 300 may have a title bar 303, which here reads "Radiologist Schedule," but may have different text in other embodiments used to view and configure other types of settings. The user interface 300 may have a table heading row 306, which may provide the headings associated with the columns 309 of the table, e.g., "Username," "Start Date," "Start Time," "End Date," and other columns. The user interface 300 may have a plurality of table rows 312, which provide the data associated with an instance of the given columns. In this case, table row 312 displays the schedule data associated with a given radiologist user. A table row 312 may be selectable and modifiable by a user, depending on proper user permissions and privileges.

Figure 4:
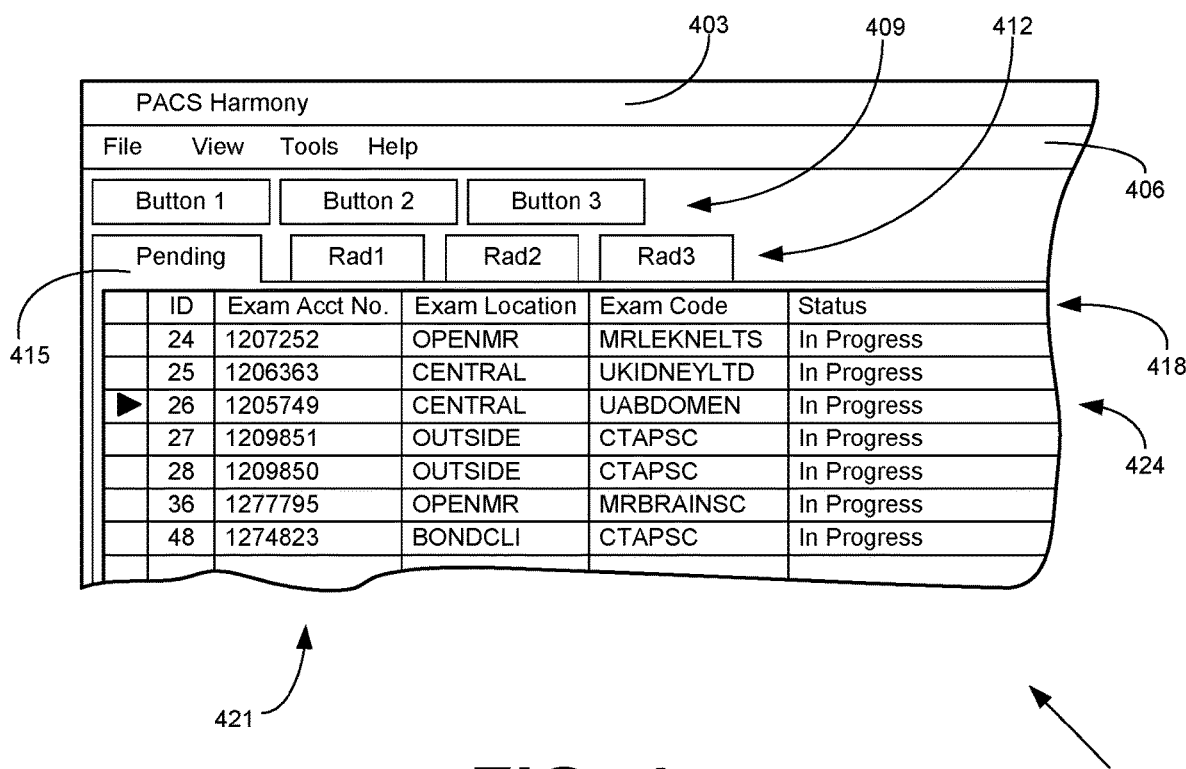

Referring next to FIG. 4, shown is one example of a user interface 400 used in an embodiment of the client application 148 (FIG. 1). The user interface 400 as shown enables a user of the client 112 (FIG. 1) to view worklists generated from assignments of medical image studies produced by the medical image study assignment application 118 (FIG. 1) executing on the server 103 (FIG. 1).

In this embodiment, user interface 400 has a title bar 403 with the title "PACS Harmony," although any appropriate title may be used. User interface 400 may have a menu 406 with any number of menus and submenus as appropriate to select features of the client application 148. User interface 400 may also have a row of buttons 409, with each button 409 enabling a feature or features, such as the ability to launch a PACS viewer 151 (FIG. 1) or other application. The user interface 400 may also have a row of tabs 412, with each tab displaying a particular worklist for a user. The embodiment shown also has a pending tab 415 containing medical image studies that have been started but not yet completed. The pending tab 415 thus gives users the ability to gauge the coming workload. The medical image studies listed in the pending tab 415 may be chosen from those having a status of, for example, in progress.

Each tab 412 may have a table heading row 418 which may provide the headings associated with the columns 421 of the table, e.g., "ID," "Exam Acct. No.," "Exam Location," "Exam Code," "Status," and other columns. The user interface 400 may have a plurality of table rows 424, which provide the data associated with an instance of the given columns. In this case, table row 424 displays the data associated with a particular medical image study. A table row 424 may be selectable and modifiable by a user, depending on proper user permissions and privileges. In particular, the status may be modifiable. In one embodiment, clicking or performing another input action on a table row 424 may launch a viewer for the selected medical image study, such as PACS viewer 151.

Figure 5:
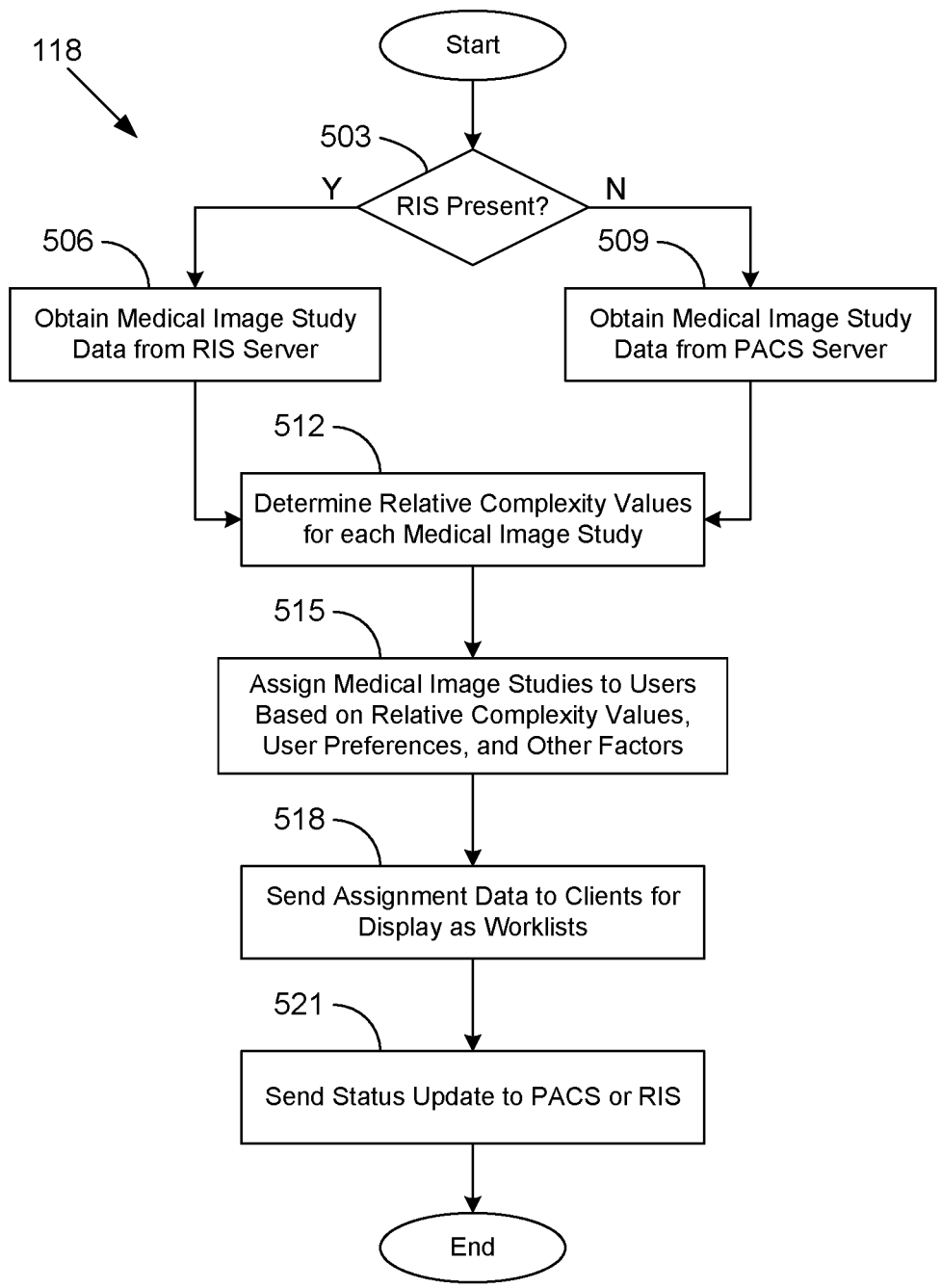
FIG. 5 is a flowchart that provides one example of functionality for a medical image study assignment application employed in the networked environment of FIG. 1 according to an embodiment of the present disclosure.

Turning now to FIG. 5, shown is a flowchart that provides one example of the operation of the medical image study assignment application 118 (FIG. 1) according to various embodiments. It is understood that the flowchart of FIG. 5 provides merely an example of the many different types of functional arrangements that may be employed to implement the operation of the medical image study assignment application 118 as described herein. As an alternative, the flowchart of FIG. 5 may be viewed as depicting an example of steps of a method implemented in the server 103 (FIG. 1) according to one or more embodiments.

To begin, in box 503, the medical image study assignment application 118 determines whether an RIS server 109 (FIG. 1) is present. This determination may be made through an automatic discovery over the network 115 or based on settings stored in system data 127 (FIG. 1). If an RIS server 109 is present, then the medical image study assignment application 118 proceeds to box 506 and obtains medical image study data from the RIS server 109. This data may be obtained through, for example, an HL7 interface.

If an RIS server is not present in box 503, then the medical image study assignment application 118 instead proceeds to box 509 and obtains medical image study data from a PACS server 106. This data may be obtained through, for example, DICOM file data.

Next, the medical image study assignment application 118, in box 512, determines the relative complexity values for each medical image study. The relative complexity values may incorporate standardized RVU designations and/or locally determined RVU designations along with other factors. Then, in box 515, the medical image study assignment application 118 assigns medical image studies to users based on relative complexity values, user preferences, and other factors. In performing the assignments, the medical image study assignment application 118 may determine a final relative weight for the medical image study incorporating coefficients for each of the factors.

Once the assignments are determined, in box 518, the medical image study assignment application 118 sends assignment data to clients 112 (FIG. 1) for display as worklists. Additionally, the assignments may be stored in assignment data 130 (FIG. 1). Finally, upon receiving a status update from a client 112 or some other event, the medical image study assignment application 118 may send a status update to a PACS server 106 and/or an RIS server 109. The medical image study assignment application 118 then ends.

Figure 6:
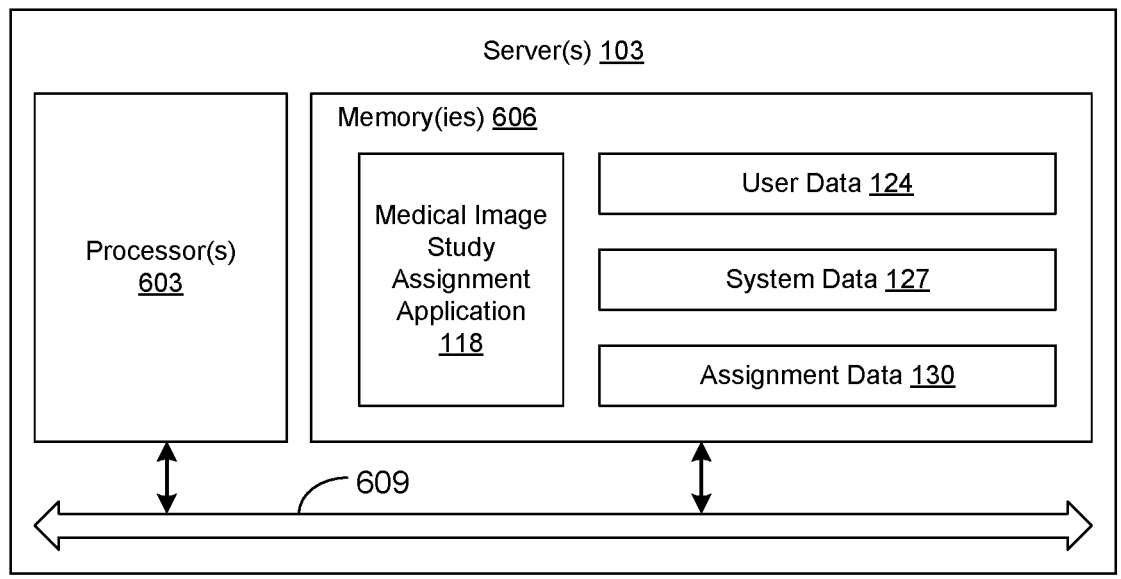
FIG. 6 is a schematic block diagram that illustrates one example of a server employed in the networked environment of FIG. 1 according to an embodiment of the present disclosure.

With reference to FIG. 6, shown is a schematic block diagram of one example of a server 103 (FIG. 1) according to an embodiment of the present disclosure. The server 103 includes a processor circuit, for example, having a processor 603 and a memory 606, both of which are coupled with a local interface 609. To this end, the server 103 may comprise, for example, a server computer with such a structure. The local interface 609 may comprise, for example, a data bus with an accompanying address/control bus or other bus structure.

Stored within the memory 606 are both executable components and data. In particular, stored in the memory 606 and executable by the processor 603 are the medical image study assignment application 118 (FIG. 1) and potentially other applications. Also stored in the memory 606 are the user data 124 (FIG. 1), system data 127 (FIG. 1), assignment data 130 (FIG. 1), and other data. In addition, a server operating system may be stored in the memory 606 and executable by the processor 603.

It is understood that there may be other applications stored in the memory 606 and executable by the processor 603. Also, other data may be stored in the memory 606 and accessed by the processor 603 associated with the operation of the medical image study assignment application 118. The medical image study assignment application 118 may be implemented using any one or a combination of a number of programming languages such as, for example, C, C++, C#, Visual Basic, VBScript, Java, JavaScript, Perl, Ruby, Python, Flash, or other programming languages.

A number of software components are stored in the memory 606 and are executable by the processor 603. In this respect, the term "executable" means a program file that is in a form that can ultimately be run by the processor 603. Examples of executable programs may be, for example, a compiled program that can be translated into machine code in a format that can be loaded into a random access portion of the memory 606 and run by the processor 603, source code that may be expressed in proper format such as object code that is capable of being loaded into a random access portion of the memory 606 and executed by the processor 603, or source code that may be interpreted by another executable program to generate instructions in a random access portion of the memory 606 to be executed by the processor 603, etc. An executable program may be stored in any portion or component of the memory 606 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 606 is defined herein as both volatile and nonvolatile memory and data storage components. Volatile components are those that do not retain data values upon loss of power. Nonvolatile components are those that retain data upon a loss of power. Thus, the memory 606 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Although the various components executed on the one or more servers 103 as described above are embodied in software or code executed by general purpose hardware as discussed above, as an alternative the various components executed on the one or more servers 103 as described above may also be embodied in dedicated hardware or a combination of software/general purpose hardware and dedicated hardware. If embodied in dedicated hardware, the various components executed on the one or more servers 103 as described above can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

The flowchart of FIG. 5 shows the architecture, functionality, and operation of an implementation of the various components executed on the one or more servers 103 as described above. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 603 in a computer system or other system. The machine code may be converted from the source code, etc. If embodied in hardware, then each block may represent a circuit or a number of interconnected circuits to implement the specified logical function(s).

Although the flowchart of FIG. 5 shows a specific order of execution, it is understood that the order of execution may differ from that which is depicted. For example, the order of execution of two or more blocks may be scrambled relative to the order shown. Also, two or more blocks shown in succession in FIG. 5 may be executed concurrently or with partial concurrence. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present invention.

Also, where the various components executed on the one or more servers 103 as described above comprise software or code, they can be embodied in any computer-readable medium for use by or in connection with an instruction execution system such as, for example, a processor 603 in a computer system or other system. In this sense, the logic may comprise, for example, statements including instructions and declarations that can be fetched from the computer-readable medium and executed by the instruction execution system. In the context of the present invention, a "computer-readable medium" can be any medium that can contain, store, or maintain the various components executed on the one or more servers 103 as described above for use by or in connection with the instruction execution system. The computer readable medium can comprise any one of many physical media such as, for example, electronic, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A system, comprising:
    at least one computing device; and
    a medical image study assignment application executable in the at least one computing device, wherein when executed the medical image study assignment application causes the at least one computing device to at least:
        obtain data describing a plurality of medical image studies from at least one medical data server, the plurality of medical image studies pending examination;

determine a relative complexity value for each of the plurality of medical image studies based at least in part on an average amount of time to perform a particular type of image study;

determine preferences of a plurality of users, the preferences corresponding to one or more coefficients comprising a numerical range;

calculate a final relative weight for each of the plurality of medical image studies based at least in part on the relative complexity value for each of the plurality of medical image studies and the one or more coefficients associated with the preferences of the plurality of users;

assign each of the plurality of medical image studies for examination by a respective user of the plurality of users based at least in part on the final relative weight for each of the plurality of medical image studies;

cause a user interface to be rendered by a client device, the user interface including a respective user worklist for each of the plurality of users; and prevent a user from viewing a particular medical image study based at least in part on a lock status associated with the particular medical image study by at least preventing access to image data associated with the particular medical image study stored in a data store.

2. The system of claim 1, wherein the lock status indicates that the particular medical image study is being viewed by another user.

3. The system of claim 1, wherein the user interface includes a pending list displaying a listing of medical image studies for which examination is pending and that are assigned to any of the plurality of users.

4. The system of claim 1, wherein the respective user worklist displays a listing of medical image studies that have been assigned to the respective user for examination.

5. The system of claim 1, wherein the preferences includes a user modality preference comprising at least one of: computed tomography, magnetic resonance imaging, mammography, nuclear medicine, radiography, positron emission tomography, and ultrasound, and the plurality of medical image studies are assigned further based at least in part on the user modality preference of the respective user.

6. The system of claim 1, wherein assignment of a medical image study of the plurality of medical image studies is not performed until a status associated with the medical image study indicates that all medical images of the medical image study are received and the medical image study is ready for examination.

7. The system of claim 1, wherein the plurality of medical image studies are assigned further based at least in part on a set of location coefficients associated with each of the plurality of users, each of the location coefficients indicating a proportion of work from a particular location that each of the plurality of the users is able to receive.

8. The system of claim 1, wherein the respective user worklist for each of the plurality of users is rendered as a respective tab in the user interface.

9. The system of claim 1, wherein the respective user worklist includes a plurality of components corresponding to a listing of medical image studies assigned to the respective user, and wherein user selection of one of the plurality of components causes a medical image study viewer to be launched for the particular medical image study.

10. A computer-implemented method, comprising:

obtaining data describing a plurality of medical image studies from at least one medical data server, the plurality of medical image studies pending examination;

determining a relative complexity value for each of the plurality of medical image studies based at least in part on an average amount of time to perform a particular type of image study;

assigning each of the plurality of medical image studies for examination by a respective user of a plurality of users based at least in part on preferences associated with the respective user and the relative complexity value determined for each of the plurality of medical image studies, the assignment not being performed until a status associated with a respective medical image study of the plurality of medical image studies indicates that all medical images of a plurality of medical images of the respective medical image study are received and the respective medical image study is ready for examination, the relative complexity value for the respective medical image study being determined at least in part by how many medical images are in the plurality of medical images;

causing a user interface to be rendered by a client device, the user interface including a respective user worklist for each of the plurality of users; and preventing a user from viewing a particular medical image study based at least in part on a lock status associated with the particular medical image study by at least preventing access to image data associated with the particular medical image study stored in a data store.

11. The method of claim 10, wherein the lock status indicates that the particular medical image study is being viewed by another user.

12. The method of claim 10, wherein the user interface includes a pending list displaying a listing of medical image studies for which examination is pending and that are assigned to any of the plurality of users.

13. The method of claim 10, wherein the respective user worklist displays a listing of medical image studies that have been assigned to the respective user for examination.

14. The method of claim 10, wherein the preferences includes a user modality preference comprising at least one of: computed tomography, magnetic resonance imaging, mammography, nuclear medicine, radiography, positron emission tomography, and ultrasound, and the plurality of medical image studies are assigned further based at least in part on the user modality preference of the respective user.

15. The method of claim 10, wherein the preferences includes a user subspecialty preference, and the plurality of medical image studies are assigned further based at least in part on the user subspecialty preference of the respective user.

16. A non-transitory computer-readable medium embodying a program executable in at least one computing device, wherein when executed the program causes the at least one computing device to at least:

obtain data describing a plurality of medical image studies from at least one medical data server, the plurality of medical image studies pending examination;

determine a relative complexity value for each of the plurality of medical image studies based at least in part on an average amount of time to perform a particular type of image study;

assign each of the plurality of medical image studies for examination by a respective user of a plurality of users based at least in part on preferences associated with the respective user and the relative complexity value determined for each of the plurality of medical image studies, the assignment not being performed until a status associated with a respective medical image study of the plurality of medical image studies indicates that all medical images of a plurality of medical images of the respective medical image study are received and the respective medical image study is ready for examination, the relative complexity value for the respective medical image study being determined at least in part by how many medical images are in the plurality of medical images;

cause a user interface to be rendered by a client device, the user interface including a respective user worklist for each of the plurality of users; and prevent a user from viewing a particular medical image study based at least in part on a lock status associated with the particular medical image study by at least preventing access to image data associated with the particular medical image study stored in a data store.

17. The non-transitory computer-readable medium of claim 16, wherein the lock status indicates that the particular medical image study is being viewed by another user.

18. The non-transitory computer-readable medium of claim 16, wherein the user interface includes a pending list displaying a listing of medical image studies for which examination is pending and that are assigned to any of the plurality of users.

19. The non-transitory computer-readable medium of claim 16, wherein the respective user worklist displays a listing of medical image studies that have been assigned to the respective user for examination.

20. The non-transitory computer-readable medium of claim 16, wherein the preferences includes a user modality preference comprising at least one of: computed tomography, magnetic resonance imaging, mammography, nuclear medicine, radiography, positron emission tomography, and ultrasound, and the plurality of medical image studies are assigned further based at least in part on the user modality preference of the respective user.

* * * * *